US006592889B1

(12) United States Patent
Stout et al.

(10) Patent No.: US 6,592,889 B1
(45) Date of Patent: Jul. 15, 2003

(54) GEL DRESSING

(75) Inventors: Edward I. Stout, Shawnee Mission, KS (US); John Phillips, Grandview, MO (US); Anthony Soria, Kansas City, MO (US); Arlen Johnson, Kansas City, MO (US)

(73) Assignee: Southwest Technologies Inc., North Kansas City, MO (US)

( * ) Notice: Subject to any disclaimer, the term of this patent is extended or adjusted under 35 U.S.C. 154(b) by 0 days.

(21) Appl. No.: 09/617,888

(22) Filed: Jul. 17, 2000

(51) Int. Cl.[7] .............................. A61K 9/70; A61L 15/00; A61L 15/16; A61F 13/00; A61F 15/00
(52) U.S. Cl. ........................ 424/443; 424/445; 424/447; 424/448; 514/944; 602/41; 602/48; 602/57; 602/61; 602/62; 602/79
(58) Field of Search .................................. 424/443, 445, 424/447, 448; 514/944; 602/41, 48, 57, 61, 62, 79

(56) References Cited

U.S. PATENT DOCUMENTS 3,612,265 A * 10/1971 Dickerson .................. 206/63.2
3,880,159 A * 4/1975 Diamond .................... 128/157
3,971,374 A * 7/1976 Wagner ...................... 128/155
4,671,267 A   6/1987 Stout ......................... 128/156
4,860,736 A * 8/1989 Kaitz et al. ................. 128/155
4,917,112 A * 4/1990 Kalt ........................... 128/156

* cited by examiner

Primary Examiner—Shelley A. Dodson
(74) Attorney, Agent, or Firm—Hovey Williams LLP

(57) ABSTRACT

A gel-type adhesive composite bandage (10) is provided which can be used in the treatment of fungus-involved or discolored toe nails, or for general wound treatment. The bandage (10) includes a base (12) having a preformed recess (16), with a humectant-containing gel (18) within the recess (16). An adhesive-coated web (14) is applied over the base (12) and gel (18). The web (14) is strippable from the base (12) with the gel (18) adhered to the web (14). In the use, the web (14) is removed from the base (12), and the exposed gel (18) is applied directly to the affected toe mail or wound. The remaining portions of the adhesive-coated web (14) is then used to maintain the web (14) and gel (18) in place. The gel (18) preferably includes a polymeric matrix having a substantial quantity of water soluble humectant (for example, glycerin) entrapped within the matrix.

21 Claims, 1 Drawing Sheet

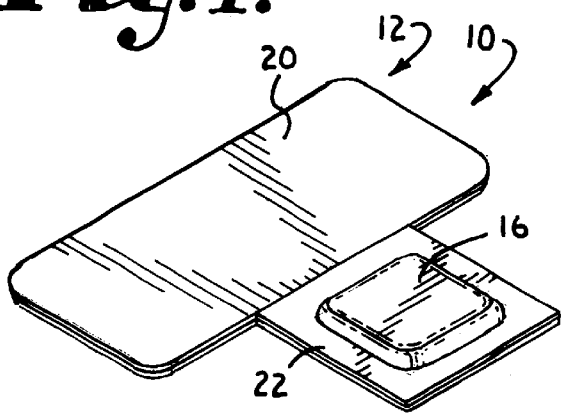
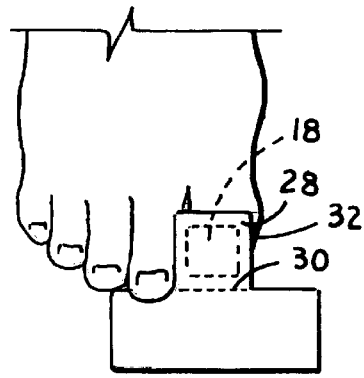
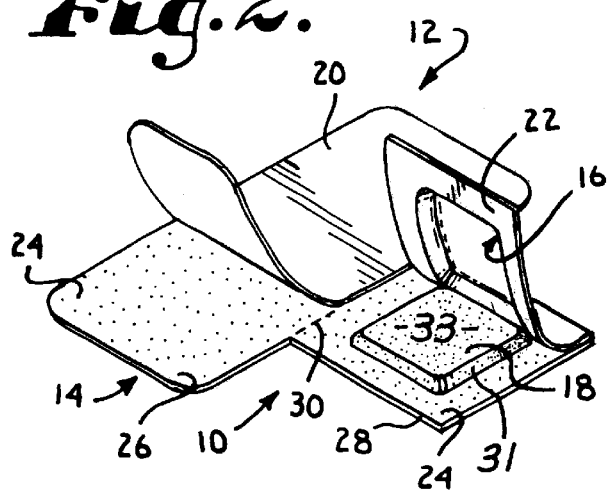
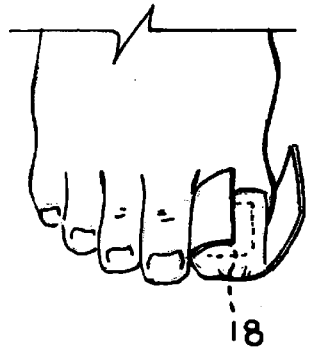
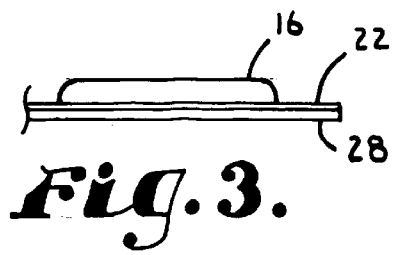

GEL DRESSING

BACKGROUND OF THE INVENTION

1. Field of the Invention

The present invention is broadly concerned with improved composite bandages for use in the treatment of fungal-infected toe nails or as a general wound dressing, wherein the bandages include a relatively stiff base with a preformed, gel-receiving recess therein together with a strippable flexible adhesive web applied over the base and gel; in use, the web is removed along with the gel and applied to form a long term bandage which promotes healing. In preferred forms, the gel includes substantial quantities of water and humectant, which enhances the healing effect.

2. Description of the Prior Art

Bandages and wraps of various types have been used by mankind for thousands of years. These have been used to cover wounds of all kinds and to provide padding and protection for inflamed tissues, for example. The goal of such uses is to prevent or ameliorate infection, and to promote rapid healing while providing a measure of pain relief.

Simple cotton or felt-type bandages have long been used, but these are at best crude expedients. In more recent times it has been proposed to provide therapy wraps, compresses and bandages which make use of gel materials. For example, U.S. Pat. No. 4,671,267 describes gel-based therapy wraps useful for treating wounds, injured skin or for orthopedic purposes. Indeed, gels in accordance with the '267 patent (commercialized under the designation Elastogel by Southwest Technologies, Inc. of Kansas City, Mo.) have proven to be particularly effective as wound and burn treatment agents. Additional gel materials are described in U.S. Pat. Nos. 4,055,188, 4,092,982 and 4,243,041.

While such gel-type bandages and the like are highly successful, in many instances rather complex wraps or attachment devices need to be provided in order to hold the gel in proper contact with a treatment site. Further, manufacturing constraints have made it difficult to provide, on an economical basis, bandage products having the otherwise desirable gel materials as a part thereof.

SUMMARY OF THE INVENTION

The present invention overcomes the problems outlined above and provides greatly improved bandage products useful for many purposes. The composite bandages of the invention broadly include base having a preformed pocket or recess therein which receives a humectant-containing gel, together with a flexible adhesive-coated web applied over the base and gel. The web is strippable from the base to give a bandage which can be applied to the skin, with the gel adhering to the web.

In preferred forms the base is formed of a shape-retaining, somewhat flexible synthetic resin material such as polystyrene, polyester or polycarbonate. During initial manufacturing steps the base material is cut to size and thermoformed to give the desired gel-receiving recess. In order to facilitate stripping of the web, the base may have a release agent (i.e., silicone-based) on the face thereof contacted by the web, either by surface coating or impregnation of the base material. The flexible web is usually fabricated from any one of a number of readily available adhesive tapes used for medical purposes.

The preferred gel contains a synthetic resin matrix with substantial quantities of water and humectant entrapped therein. Advantageously, gels described in U.S. Pat. No. 4,671,267 (which is incorporated by reference herein) are used in the bandages of the invention. Such gels can be readily cast in appropriate shapes and sizes, and provide a marked healing effect on a variety of wounds and the like. Moreover, it has been discovered that these gels, particularly when used in the bandages of the invention, give unexpectedly superior results when used in the treatment of discolored or fungus-involved toe nails. In the past, toe nail treatments have involved removal of the nail to eliminate fungi, which is a painful and time-consuming regimen. However, through use of the gel materials and bandages of the invention, complete recovery in the form of fungi elimination and return to proper coloration is achieved simply by application of the gel directly on the toe nail in a covering wrap or bandage for a period of several days (e.g., from about 2–10 days is usually sufficient). The hydration and humectant treatment afforded by this technique is believed to be responsible for these remarkable results.

The composite bandages of the invention can be economically produced using simple stepwise production methods. In practice, the base synthetic resin is cut into "sheets" and preformed using vacuum-forming techniques; typically, a number of individual bases are produced simultaneously on one sheet. The formed sheet is then moved to a gel filling station, where the appropriate amount of gel precursor liquid is poured or injected into each base recess. The gel material is then allowed to cure within the recesses, forming flexible but self-sustaining gel bodies. Finally, an adhesive web is applied over each sheet so as to essentially cover the bases and to contact the respective gel bodies. The individual bases are then cut to size and shape. The completed composite bandages can then be packaged and sterilized.

BRIEF DESCRIPTION OF THE DRAWINGS

FIG. 1 is a perspective in view of a composite bandage in accordance with the invention;

FIG. 2 is a perspective in view similar to that of FIG. 1, but illustrating the separation of the base and adhesive-coated web of the composite bandage;

FIG. 3 is a fragmentary side view of the gel-supporting portion of the composite bandage illustrated in FIGS. 1 and 2;

FIG. 4 is a top view showing the initial step in application of the bandage of FIG. 1 to the great toe of a person; and FIG. 5 is a view similar to that of FIG. 4, but illustrating the final steps in application of the bandage to the person's toe, wherein segments of the adhesive-coated web are overlapped to complete application of the bandage.

DETAILED DESCRIPTION OF THE PREFERRED EMBODIMENT

Turning now to the drawings, a composite bandage 10 in accordance with the invention broadly includes a base 12 together with an adhesive-coated web 14 applied to the base 12. The base 12 has a preformed recess 16 therein which is adapted to hold a quantity of gel 18, with the web 14 being strippable from the base 12 and gel 18 for application to a body part.

In more detail, the base 12 is preferably formed of substantially shape-retaining synthetic resin material such as high-impact polystyrene. In the illustrated embodiment, the base 12 is made up of an elongated, primary section 20 together with a shorter, transverse section 22. In this fashion, the overall base 12 is somewhat T-shaped. It will also be seen that the sections 20, 22 are separate from each other. The base 12 is preferably fabricated from a substantially shape-retaining synthetic resin material such as polystyrene. In order to facilitate removal of the web 14 from the base 12, the faces of the sections 20, 22 adjacent the web 14 are coated with a silicone release agent. As illustrated, the transverse section 22 is provided with the recess 16. This is preferably accomplished by a thermoforming of the base 12 during manufacture.

The web of 14 is designed to overlay the base 12 in covering relationship to the gel 18 within recess 16. The web 14 is a conventional medical tape such as the MED716 tape sold by Avery Dennison Specialty Tape Division of Painesville, Ohio. The web 14 has an adhesive coating 24 applied to the inner face thereof as best seen in FIG. 2. In addition, it will be seen that the web 14 has a primary section 26 and a secondary section 28 which are complemental with the corresponding base sections 20, 22; however, the web sections 26, 28 are separated by a perforation line 30. The web 14 is strippable from the base 12 with the self-sustaining gel quantity 18 adhered thereto and protruding outwardly therefrom. The gel presents a circumferential sidewall 31 and a top wall 33 spaced from the web.

The gel 18 comprises a polymeric matrix having acrylic or acrylamide monomer moieties with a substantial amount of water soluble humectant therein. The humectant is preferably selected from the group consisting of glycerin, ethylene glycol, propylene glycol, dimethyl sulfoxide, and a dimethyl formamide. The humectant is preferably present at a level of about 20–85% by weight in the gel body, and more preferably from about 50–75% by weight. The preferred polymeric matrix is selected from the group consisting of polymers, copolymers, and terpolymers containing acrylic acid or acrylamide and monomer moieties, and most preferably is a polymer of acrylamide.

Accordingly, while a wide variety of gel formulations can be used to good effect in the invention, it has been found that certain specific components and amounts arranges give the most satisfactory results. The following table sets forth the most preferred formulations, with approximate ranges:

TABLE

| Constituent | Preferred[1] | Range[1] |
| --- | --- | --- |
| Citric acid | 0.02 | 0.01–0.10 |
| Ammonium persulfate | 0.04 | 0.01–0.2 |
| N,N methylene-bisacrylamide | 0.08 | 0.02–0.15 |
| [2]acrylamide | 14.42 | 10.0–25.0 |
| [2]water | 14.42 | 10.0–50.0 |
| glycerin | 71.00 | 50.0–85.0 |
| [3]Super absorbant | 0.02 | 0.10–0.60 |

[1]All data in percentages by weight
[2]Premixed as a 50% by weight solution of acrylamide and water
[3]Hydrolyzed starch-acrylonitrile graft copolymer (an optional ingredient), described in U.S. Pat. No. 3,935,009

While the above table sets forth the preferred constituents and ranges, those skilled in the art will appreciate that the invention is not so limited. For example, while the preferred crosslinking agent is N. N methylene-bisacrylamide (MBA), other types of crosslinking agents can be employed such as N-methylolacrylamide, allyl methacrylate, and ethylene glycol dimethacrylate. Moreover, while ammonium persulfate is a suitable initiator for the polymerization reaction, the use of an initiator is not essential. Finally, while acrylamide is the preferred matrix-forming material, other similar materials can also be used, such as acrylic acid. In such cases, the acrylic acid should be used at a level of from about 10–20% by weight, humectant at a level of from about 20–80% by weight, water at a level of from about 20–70% by weight, MBA at a level of from about 0.02 to 0.04% by weight. The most preferred ranges are from about 14–18% acrylic acid, from about 50–76% humectant, from about 8–22% water, and from about 0.01–0.3% crosslinking agent.

Those skilled in the art will also appreciate that by proper selection of monomer and by varying the ratio of monomer (or monomers) relative to the crosslinking agent and humectant, the hardness and toughness of the gel material may be altered and controlled. Accordingly, if relatively high moisture absorption characteristics are desired, the gel should be formulated to have a high percentage of humectant and a relatively low percentage of crosslinking agent in order to produce a soft, relatively rubbery gel. If more firmness is required, the amount of humectant may be reduced, whereas the amount of crosslinking agent should be increased.

In fabricating the gel mixtures using the above constituents, is desirable to mix or stir such constituents at a temperature of above about 65° F., whereupon the liquid mixture is placed within the recess 16 and allowed to set for at least about ½ hour to 45 minutes.

The gel 18 should have a thickness of from about 1/32 to about 3/8 inch, and more preferably from about 1/16 to 1/4 inch, in the context of bandages illustrated in FIGS. 1–5. However, this parameter is not critical, and different types or styles of bandages would commonly be provided with the gel bodies of different thicknesses.

The use of bandage 10 is illustrated in FIGS. 4 and 5, where a person's great toe is being bandaged. First, the base sections 20, 22 are stripped from the web 14 leaving a generally T-shaped bandage with a body of gel 18 secured to and protruding outwardly from the transverse section 28 of the web 14. Next, the gel body 18 is applied over the person's great toe 32, with the gel body in direct contact with the toe nail. Thereupon, the primary web section 26 is folded under the great toe, and the laterally projecting portions of the section 26 are folded upwardly and overlapped atop the transverse web section 28 to form a completed bandage. It has been found that the use of a relatively high moisture vapor transmission web 14 serves to enhance healing. It is believed that such material facilitates penetration of the humectant into the toe nail because, when the web is wetted, the moisture is readily transmitted through the web.

It will be appreciated that the bandage 10 could be used in other contexts as well. For example, the transverse section 28 may be separated along perforation line 30 when applied to a wound, for example. Thereupon, the separated primary web section 26 can be used in the manner of adhesive tape to hold the gel-supporting transverse section 28 in place.

The bandage 10 may be left in place for up to 7–10 days. The presence of humectant within the gel 18 assures that the toe nail or other wound remains adequately hydrated to promote rapid healing. In the case of discolored or fungal-involved toe nails, the bandage 10 has been found to essentially completely eliminate the condition, usually after repeated applications with new bandages.

While the bandage 10 has been shown in a generally T-shaped form, the invention is not so limited. That is, the web and adhered base can be of virtually any shape or configuration, such as square, circular or rectangular. Such bandages can be used for treatment of wounds or the like on the trunk or limbs of a person.

It will also be appreciated that bandages in accordance with the invention can be economically produced on a production-line basis. In practice, a starting base sheet is first vacuum formed to present a plurality of recesses. (Alternately, other thermo- forming processes involving heat, pressure and/or vacuum can be used.) Then, the base sheet is advanced and liquid gel precursor is injected into the recesses. Once the gel is adequately cured within the recesses, an adhesive-coated web is applied over the sheet and all of the recesses containing the cured gel. Thereupon, the composite is cut to provide individual bandages which are then conventionally packaged. It will be appreciated that automated, roll-fed form, fill and seal packaging equipment could be used to achieve even greater efficiencies.

We claim:

1. A composite bandage comprising:

a base presenting a recess;

a quantity of self-sustaining gel within said recess; and an adhesive-coated web adhesively secured to said base and covering and engaging said gel, said web being strippable from said base with said self-sustaining gel quantity adhered thereto and protruding outwardly therefrom, said gel presenting a circumferential sidewall and a top wall spaced from said web, said web adhesive operable to maintain the web in place on skin with said gel beneath the web.

2. The bandage of claim 1, said base formed of synthetic resin material.

3. The bandage of claim 1, said recess formed by vacuum forming.

4. The bandage of claim 1, said web generally T-shaped and presenting a short leg and a longer transverse leg with said gel adhered to said short leg.

5. The bandage of claim 1, said gel having a matrix including polymerized acrylic acid or acrylamide monomer moieties and a water soluble humectant entrapped within said matrix.

6. The bandage of claim 5, said gel comprising from about 10–25% of said polymeric matrix from about 10–50% by weight water, and a substantial quantity of a humectant entrapped within said matrix.

7. The bandage of claim 6, said humectant being present at a level of from about 20–85% by weight in said gel body.

8. The bandage of claim 6, said humectant being present from the group consisting of glycerin, ethylene glycol, propylene glycol, dimethyl sulfoxide and dimethyl formamide.

9. The bandage of claim 6, said matrix comprising a polymer of acrylamide.

10. A method of forming a composite bandage comprising the steps of:

providing a base presenting a recess;

filling said recess with a quantity of self-sustaining gel material; and applying an adhesive-coated web over said base and recess, and causing the web to adhere to the base and gel material.

said web being strippable from said base with said self-sustaining gel quantity adhered thereto and protruding outwardly therefrom, said gel presenting a circumferential sidewall and a top wall spaced from said web.

11. The method of claim 10, said gel material having a water soluble humectant entrapped within a polymeric matrix having therein acrylic acid or acrylamide monomer moieties.

12. The method of claim 11, said gel material comprising from about 10–25% of said polymeric matrix from about 10–50% by weight water, and a substantial quantity of a humectant entrapped within said matrix.

13. The method of claim 11, said humectant being present at a level of from about 20–85% by weight in said gel material.

14. The method of claim 11, said humectant being selected from the group consisting of glycerin, ethylene glycol, propylene glycol, dimethyl sulfoxide and dimethyl formamide.

15. The method of claim 11, said matrix comprising a polymer of acrylamide.

16. The method of claim 10, including the step of vacuum forming a recess in a relatively stiff synthetic resin body to provide said base.

17. The bandage of claim 1, said gel having a thickness of from about 1/32 to 3/8 inch.

18. The bandage of claim 17, said thickness being about 1/16 to 1/4 inch.

19. The bandage of claim 1, said base having a release agent on the surface thereof engaged by said web.

20. A method of treating a discolored or fungus-infected toe nail comprising the steps of applying directly to said toe nail a humectant-containing gel, and maintaining said gel in place on said toe nail for a period of several days.

21. The method of claim 20, including the step of wrapping said gel within a wrap which holds the gel in place on said toe nail, said wrap including an adhesive-coated web which adheres to the skin of the toe adjacent said toe nail.

* * * * *